(12) United States Patent
Dirauf et al.

(10) Patent No.: US 9,314,647 B2
(45) Date of Patent: Apr. 19, 2016

(54) HOLDING ARM AND ARRANGEMENT FOR SUPPORTING DIAGNOSTIC IRRADIATION IN RADIATION THERAPY APPLICATIONS

(75) Inventors: Franz Dirauf, Ebensfeld (DE); Franz Fadler, Hetzles (DE); Christian Ziegler, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 477 days.

(21) Appl. No.: 13/209,144

(22) Filed: Aug. 12, 2011

(65) Prior Publication Data

US 2012/0205555 A1 Aug. 16, 2012

(30) Foreign Application Priority Data

Aug. 12, 2010 (DE) .......................... 10 2010 034 101

(51) Int. Cl.
| | |
|---|---|
| *A61N 5/00* | (2006.01) |
| *F16M 13/00* | (2006.01) |
| *A61N 5/10* | (2006.01) |
| *A61B 6/00* | (2006.01) |

(52) U.S. Cl.
CPC ............ *A61N 5/1049* (2013.01); *A61B 6/4441* (2013.01); *A61N 5/1081* (2013.01); *A61N 2005/1061* (2013.01)

(58) Field of Classification Search
CPC .................... A61N 5/1081; A61N 2005/1054; A61N 5/1049; A61N 5/1048; A61N 2005/1061; A61B 6/4441
See application file for complete search history.

(56) References Cited

U.S. PATENT DOCUMENTS

| | | | | |
|---|---|---|---|---|
| 5,577,094 A | * | 11/1996 | Fudamoto ............ | A61N 5/1081 378/65 |
| 5,782,623 A | * | 7/1998 | Brox .............................. | 418/153 |
| 6,839,404 B2 | | 1/2005 | Clark et al. | |
| 6,888,919 B2 | * | 5/2005 | Graf ................... | 378/65 |
| 7,418,080 B2 | * | 8/2008 | Fadler ............. | 378/65 |
| 7,448,800 B2 | * | 11/2008 | Steger et al. .................. | 378/193 |
| 2003/0007601 A1 | * | 1/2003 | Jaffray et al. ................... | 378/65 |
| 2003/0101513 A1 | | 6/2003 | Wong | |
| 2005/0281389 A1 | | 12/2005 | Kusch et al. | |
| 2007/0081632 A1 | | 4/2007 | Fadler | |
| 2007/0230660 A1 | * | 10/2007 | Herrmann ....................... | 378/65 |
| 2008/0191142 A1 | | 8/2008 | Pedroni | |
| 2010/0054414 A1 | | 3/2010 | Herrmann | |
| 2010/0239073 A1 | | 9/2010 | Eaves | |

FOREIGN PATENT DOCUMENTS

| | | |
|---|---|---|
| CN | 1947813 A | 4/2007 |
| DE | 10 2004 062 473 A1 | 4/2006 |

OTHER PUBLICATIONS

German Office Action dated Jun. 24, 2011 for corresponding German Patent Application No. DE 10 2010 034 101.0 with English translation.
Chinese Office Action dated Jan. 6, 2015 for corresponding Chinese Patent Application No. 201110300069.2, with English translation.

* cited by examiner

*Primary Examiner* — David J Makiya
*Assistant Examiner* — Dani Fox
(74) *Attorney, Agent, or Firm* — Lempia Summerfield Katz LLC

(57) ABSTRACT

The present embodiments relate to a holding arm for a detector that may be positioned on a first arm end or a diagnostic beam source that may be positioned on the first arm end. The present embodiments also relate to a radiation therapy arrangement with the holding arm. The holding arm may be positioned in a region of a second arm end in an emitter head region of a radiation therapy system and is essentially curved.

15 Claims, 10 Drawing Sheets

HOLDING ARM AND ARRANGEMENT FOR SUPPORTING DIAGNOSTIC IRRADIATION IN RADIATION THERAPY APPLICATIONS

This application claims the benefit of DE 10 2010 034 101.0, filed on Aug. 12, 2010.

BACKGROUND

The present embodiments relate to a holding arm and an arrangement with the holding arm provided for a radiation therapy device.

The use of radiation to destroy diseased tissue (e.g., a tumor) is a widely used procedure in therapeutic medicine. Systems that use high-energy electromagnetic radiation may be employed. Such a system is described by way of example in U.S. Pat. No. 6,839,404 B2.

During the course of radiation therapy, it may be desirable to use the same device to perform diagnostic irradiation. This may be used to monitor and better locate the tumor to be irradiated around the time of or during therapeutic irradiation. In the abovementioned publication, radiation therapy is provided with a Portal Imaging System for this purpose. This system allows "in-line" imaging. The radiation generated by the therapy device for tissue treatment (e.g., MV radiation generated using a linear accelerator) is also used for diagnostic purposes and is detected using a detector after penetrating the object. This allows therapeutic and diagnostic radiation to be supplied in an essentially parallel manner and from the same source, which represents a significant simplification. The source may be adapted for low-energy radiation (e.g., kV range) by using, for example, a carbon target instead of a tungsten target. This procedure is also described in the publication "In-Line kView Imaging" by Siemens AG.

According to a development of the "in-line" concept, an antiparallel rather than a parallel diagnostic beam is used. A beam source replaces the detector. Additionally, a detector for the diagnostic radiation is disposed in a region of an exit point of the therapeutic radiation for the diagnostic application. This detector for diagnostic irradiation, which is positioned in the beam path of the therapeutic radiation, is removed for therapeutic irradiation (e.g., folded back). This procedure with a separate beam source allows the diagnosis to be performed with a lower dose (e.g., kV range), without the therapeutic beam source having to be adapted for low-energy radiation. Both procedures (e.g., parallel and antiparallel irradiation) have the advantage that the system as a whole is not rotated for the recordings to switch between the positions for therapeutic and diagnostic radiation.

Radiation therapy systems, as shown, for example, in FIG. 1 and FIG. 2, may have only one degree of freedom (e.g., rotation of the system as a whole). The irradiation device, therefore, is aligned with an isocenter (e.g., a tumor position) by positioning the patient table, for example. Positioning using the patient table is not ideal, primarily because positioning using the patient table is troublesome for the patient on the table, who may be in physically poor shape. Also, the system shown in FIG. 1 and FIG. 2 allows a tumor to be irradiated from different directions in a limited fashion.

SUMMARY AND DESCRIPTION

There is a need for radiation therapy methods that allow more flexible positioning of a source for therapeutic radiation and new therapy concepts, with these same functions also being retained with respect to diagnostic irradiation.

The present embodiments may obviate one or more of the drawbacks or limitations in the related art. For example, diagnostic irradiation for a more flexible radiation therapy system kinematic may be provided.

The present embodiments are based on the consideration that for a more flexible irradiation system kinematic, a therapeutic radiation source may be given additional degrees of freedom. A radiation head or a beam generation unit with a therapeutic beam source, which allows flexible positioning, is provided. The radiation head includes the radiation source and any support units. In order to integrate diagnostic applications efficiently in a system with a flexible radiation head, an arm that may be positioned on the radiation head is provided (e.g., in a region of the therapeutic radiation source). The advantage of such a design is that when the head is moved in any way by way of the arm (e.g., an essentially rigid arm), an apparatus fastened to the other end of the arm also executes the movements; in other words, with flexible head positioning, an apparatus positioned on the arm is moved correspondingly by way of a rigid connection to the head. In one embodiment, the arm may be connected to the radiation head in a region of one end and is intended to hold a device used for the diagnostic application at the other end. The device may be a detector that, for example, detects radiation from the therapeutic radiation source (e.g., in-line imaging). In one embodiment, the device may be at least one beam source that generates radiation, which is detected by a detector that may be positioned for this purpose in a region of the beam exit point of the radiation head. A plurality of sources or a multi-emitter source may be provided, for example, so that images may be recorded in an angle range from different positions, thereby allowing 3D reconstruction. One embodiment of the arm for a detector or beam source (e.g., also referred to in the following as a holding arm) may be essentially curved. "Essentially" may be with the exception of one end segment or with the exception of both end segments. In one embodiment, a regular curvature may be provided. This has the advantage that the arm may be fastened to the emitter head such that the arm may be moved in and out in the manner of an orbital movement or circular movement. This allows recordings to be made at different angles (e.g., for 3D reconstruction) and allows the arm to be pulled in or retracted into a position, in which the arm is not in the way for purely therapeutic applications or if the device is not in use (e.g., a park position).

According to one embodiment, the arm has at least one joint (e.g., two joints) in a region of the detector or beam source. In one embodiment, an arm segment that is not curved in the region is provided. The arm segment is configured as a jointed arm or a pivot arm, so that the device held (e.g. a detector or a emitter) may be positioned more efficiently with additional degrees of freedom. The system for suspending the curved or C-shaped arm from the emitter head may also be fastened to a pivot axis to achieve more advantageous positioning and a favorable collision-free movement sequence.

DETAILED DESCRIPTION OF THE DRAWINGS

Figure 1:
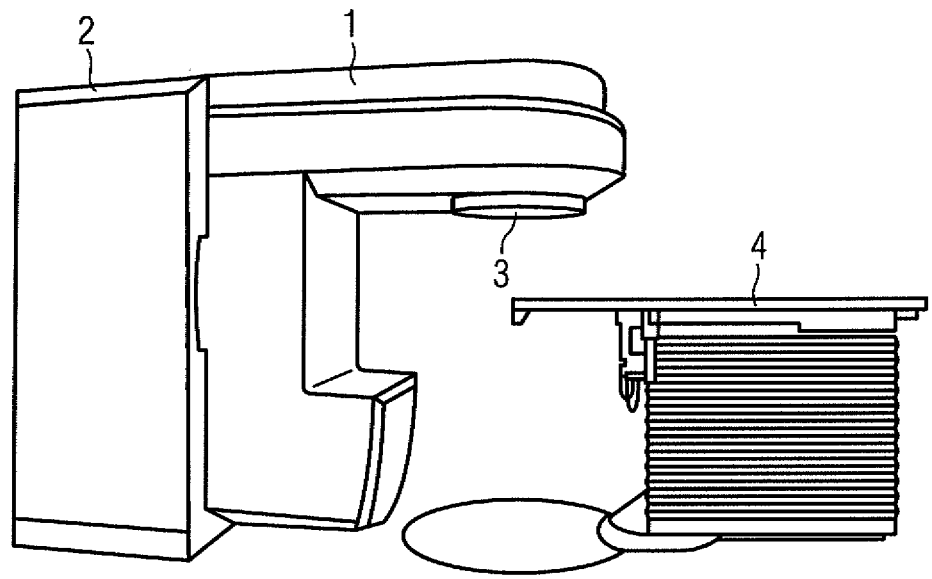
FIG. 1 shows a therapy system.
Figure 2:
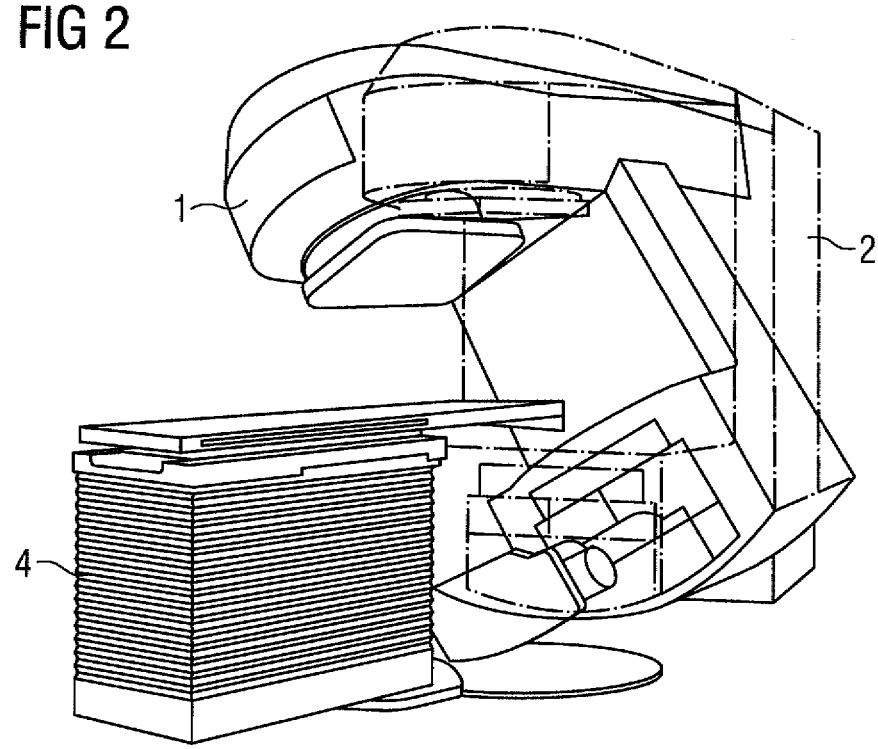
FIG. 2 shows a pivoted therapy system.

FIG. 1 and FIG. 2 show a therapy system, where one degree of freedom (e.g., rotation) of a beam source 3 is provided. Further degrees of freedom are realized by patient positioning using a patient table 4.

Figure 3:
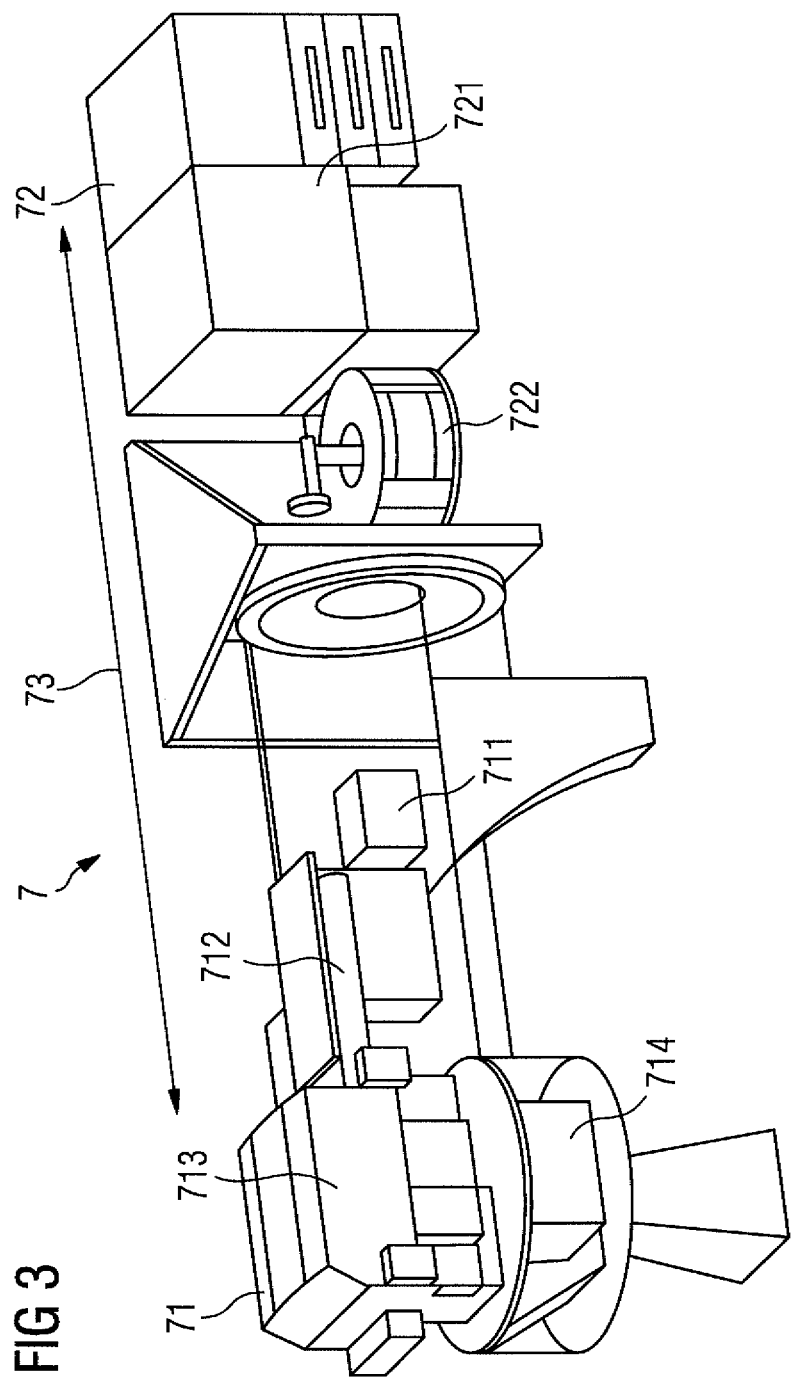
FIG. 3 shows a beam generation unit for the positioning of one embodiment of an arm.

FIG. 3 shows details of a beam generation unit 7 (e.g., an emitter unit). The emitter unit 7 allows the introduction of additional degrees of freedom, as set out in more detail with reference to FIG. 4.

The emitter unit 7 include a first part 71 and a second part 72. The first part 71, which may also be referred to as an emitter head, includes typical functions for beam generation. The functions for beam generation include, for example, a circulator 711, a linear accelerator 712, a magnet for shielding and beam deflection 713, and a multileaf collimator 714. The second part 72 essentially includes components for energy generation and modulation 721 and a magnetron 722 (e.g., a vacuum tube for generating electromagnetic radiation in the microwave range). The magnetron 722 represents a high-frequency generator. The structure of the radiation unit allows the radiation unit to be employed efficiently in a more flexible kinematic.

The emitter unit 7 has a longish shape. A longitudinal extension (e.g., arrow 73) defines an extension that is referred to in the following as a direction of longitudinal extension or an extension direction of the emitter unit or the emitter head.

Figure 4:
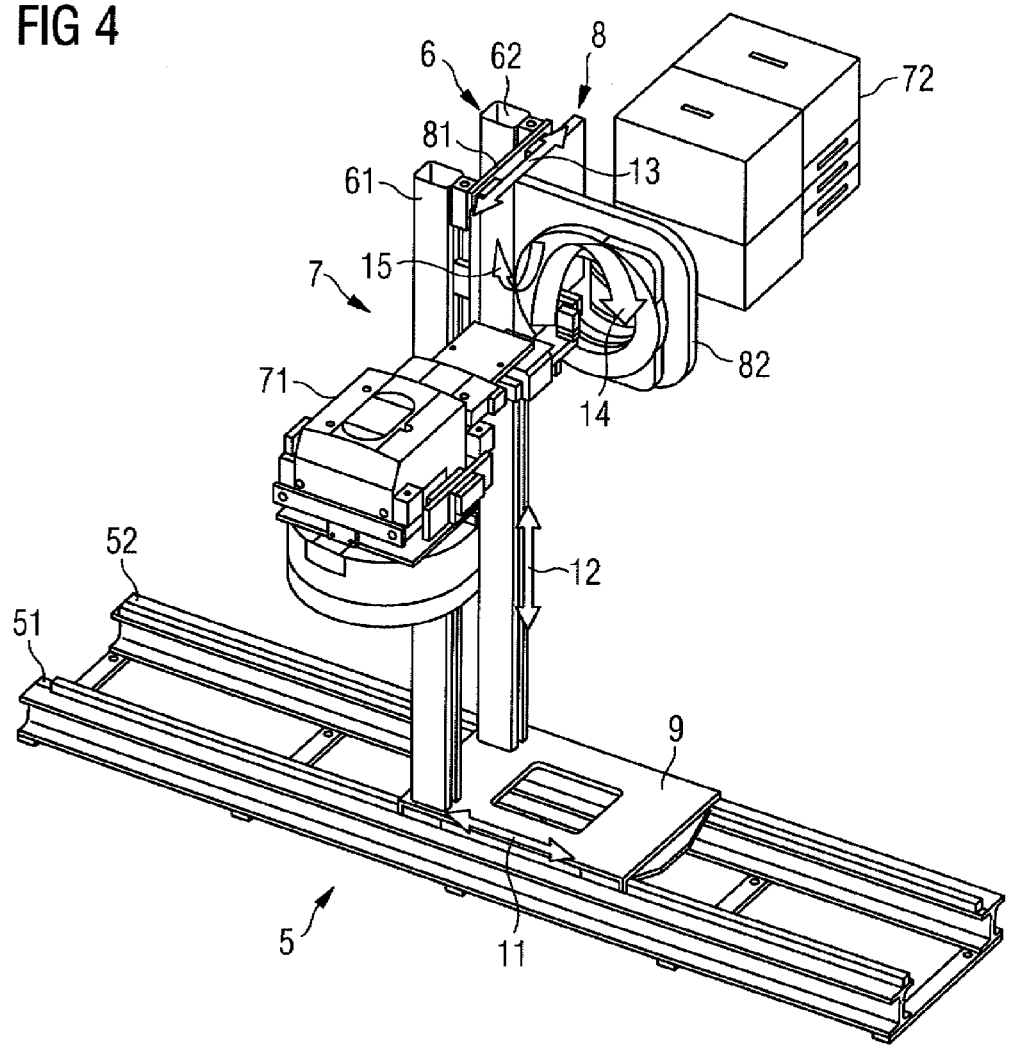
FIG. 4 shows one embodiment of a suspension system and degrees of freedom of a radiation head.

FIG. 4 shows the kinematic without cladding (in contrast to FIGS. 1 and 2), in order to be able to better follow a mode of operation. The apparatus as a whole rests on a floor guide 5 formed with two rails 51 and 52. Alternatively, a ceiling guide may be provided. Positioned on the two rails 51 and 52 is a carriage 9 that supports a vertical guide 6. The vertical guide 6 is formed with two rails 61 and 62. A drive unit for the irradiation apparatus may be provided between the two rails 61 and 62 or on the carriage 9. A support element 8 is provided to support the emitter unit 7 described in more detail in FIG. 3. The support element 8 may be moved along the vertical guide 6. This is realized, for example, in that the support element 8 is formed with a carriage 81, on which a plate 82 with a round opening is disposed in a perpendicular manner. The emitter unit 7 is disposed on this plate 82. The opening in the plate 82 is provided for the passage of connections between the first part 71 and the second part 72 of the emitter unit 7. The connections may be provided for the transmission of energy (e.g., cables) and also for mechanical purposes (e.g., stability). The first part 71 and the second part 72 of the emitter unit 7 provide essentially different functions (e.g., energy generation for the second part 72 and radiation generation for the first part 71). A weight of the first part 71 and the second part 72 of the emitter unit 7 is at least partially compensated for with respect to a positioning point on the plate 82 (e.g., the configuration of the emitter unit 7 from essentially two parts reduces the load (moments occurring)).

The system shown has five degrees of freedom. One degree of freedom of displacement or translation is provided along a horizontal axis 11. This degree of freedom is realized using the carriage 9. A translation in the vertical direction 12 is realized using the vertical guide 6 and the carriage 81. A further degree of freedom is a translation along a transverse axis 13. This is realized, for example, by allowing the plate 82 to be displaced in a transverse manner on the carriage 81. The emitter unit 7 may be rotated about an essentially transverse axis (e.g., degree of freedom 14). A tilting degree of freedom 15 present in FIG. 3 in relation to a horizontal axis.

All the degrees of freedom may interact, for example, so that isocentric irradiation takes place. For example, the tilting degree of freedom 15 and the transverse degree of freedom 13 may be modified in a mutually coordinated fashion.

The present embodiments relate to the problem of how diagnostic irradiation may be realized for an irradiation system according to FIG. 4. One embodiment of a solution is shown in FIG. 5.

Figure 5:
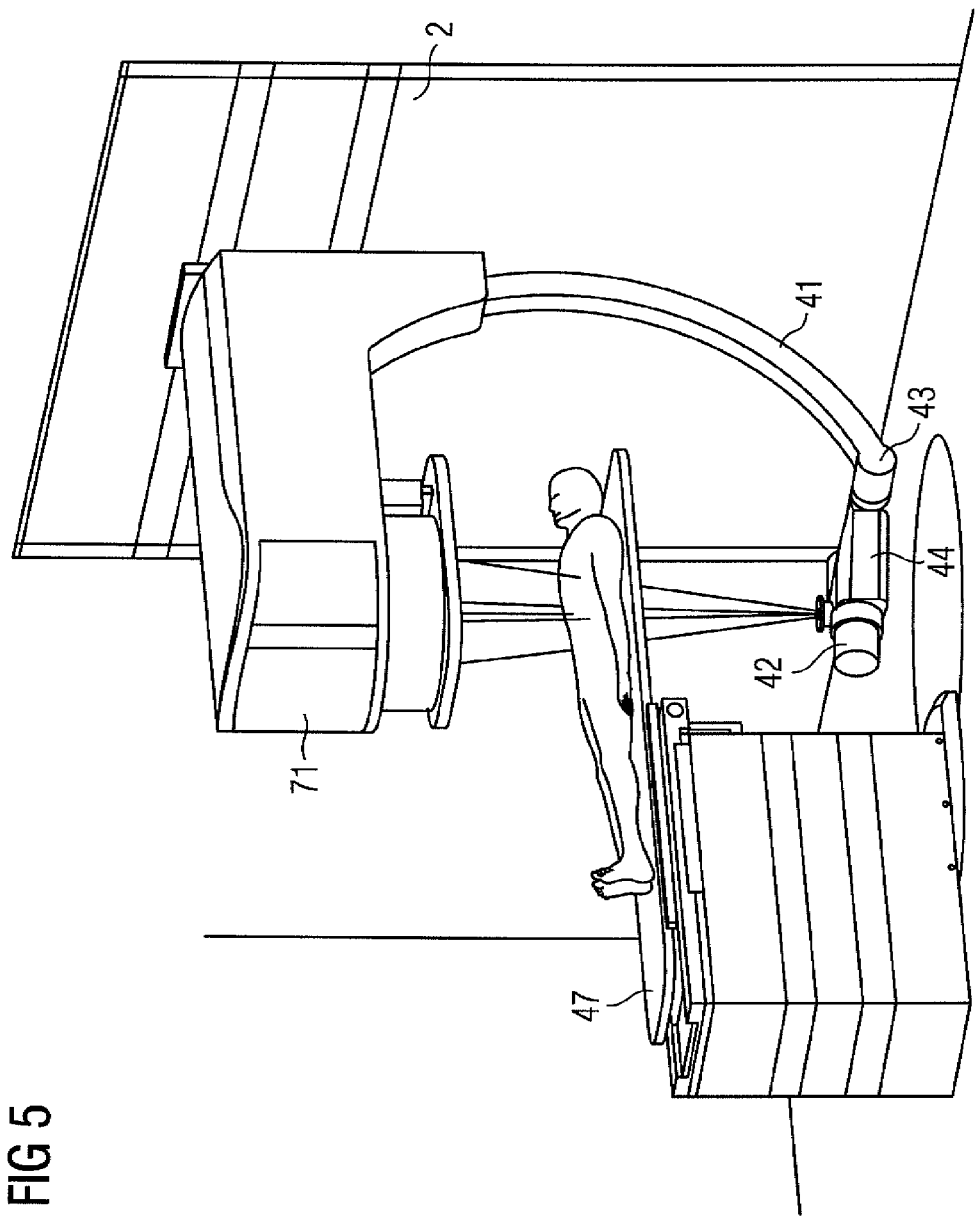
FIG. 5 shows a radiation head positioned on a gantry with one embodiment of a holding arm.

FIG. 5 shows an emitter head 71 positioned on a gantry 2. The emitter head 71 may be part of a radiation unit, as shown in FIG. 3 (see also FIG. 7). Positioned on the emitter head 71 is one embodiment of a holding arm 41 that is essentially embodied as a C-arm. The holding arm 41 extends essentially in a plane defined by the vertical and an extension direction of the emitter head 71 or a patient couch 47.

Figure 6:
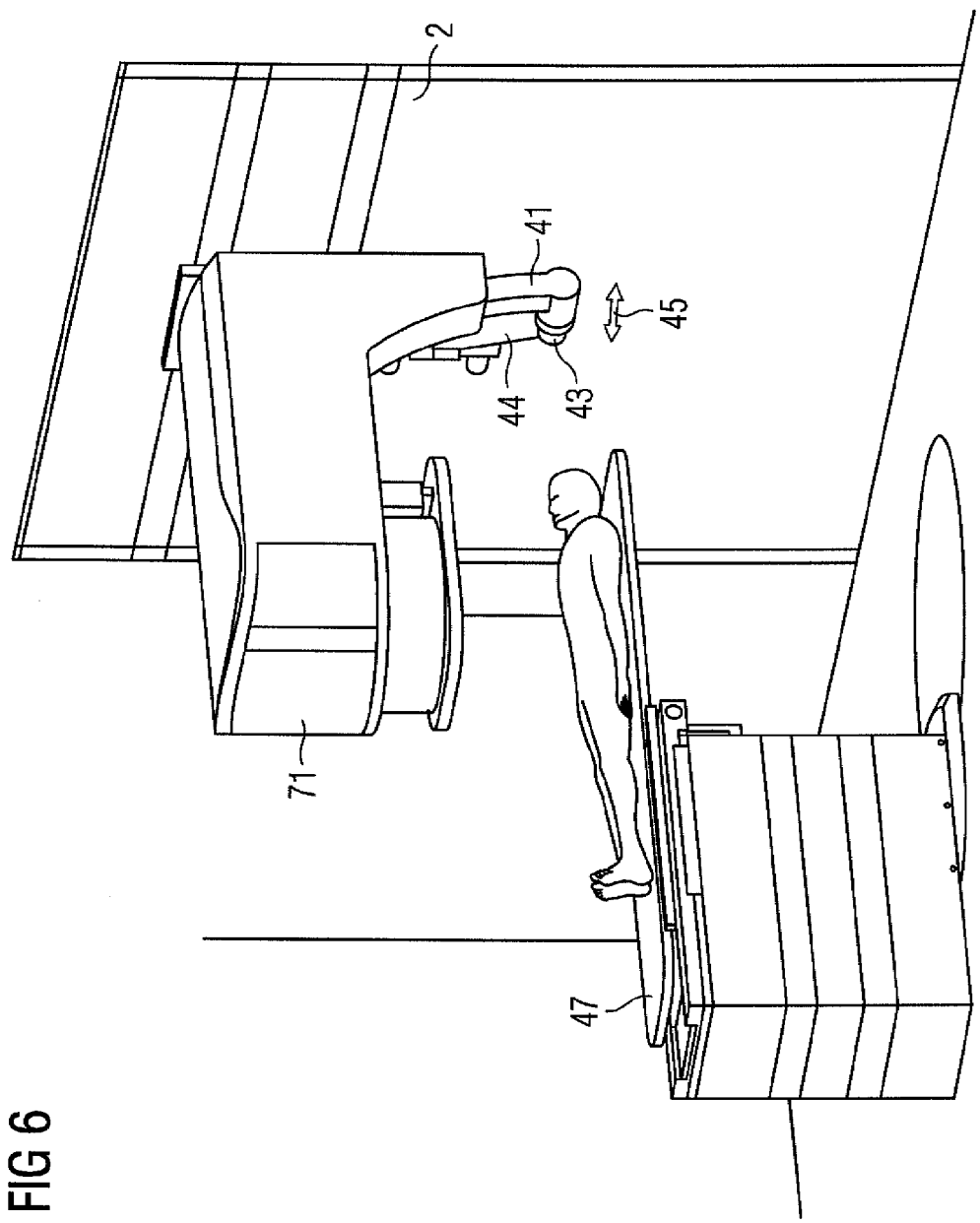
FIG. 6 shows an emitter head positioned on a gantry with one embodiment of a holding arm in a park position.

The C-arm also includes a joint 43, to which a jointed arm segment 44 is connected. The jointed arm segment 44 supports a beam source 42 (e.g., kV radiation). The joint 43 has a rotation axis that is oriented horizontally and perpendicular to a direction defined by a longitudinal extension of the emitter head or of the emitter unit according to FIG. 3. The longitudinal extension of the emitter head, for example, is parallel to a patient couch direction. The joint 43 also provides that the jointed arm segment 44 is offset laterally (e.g., in a direction of the rotation axis). This applies to the positioning of the holding arm 41 in a park position. The park position is shown in FIG. 6. In FIG. 6, a curved part of the holding arm 41 is retracted and is essentially accommodated in cladding of the emitter head 71. "Essentially" may be apart from a projecting end segment. The jointed arm segment 44 is folded up using the joint 43 and comes to rest adjacent to a lower extension of the cladding on account of the offset 45. In this position, the holding arm 41 disappears almost completely, so that the holding arm 41 takes up little space and does not get in the way even when handled by operators or during therapeutic applications.

Figure 7:
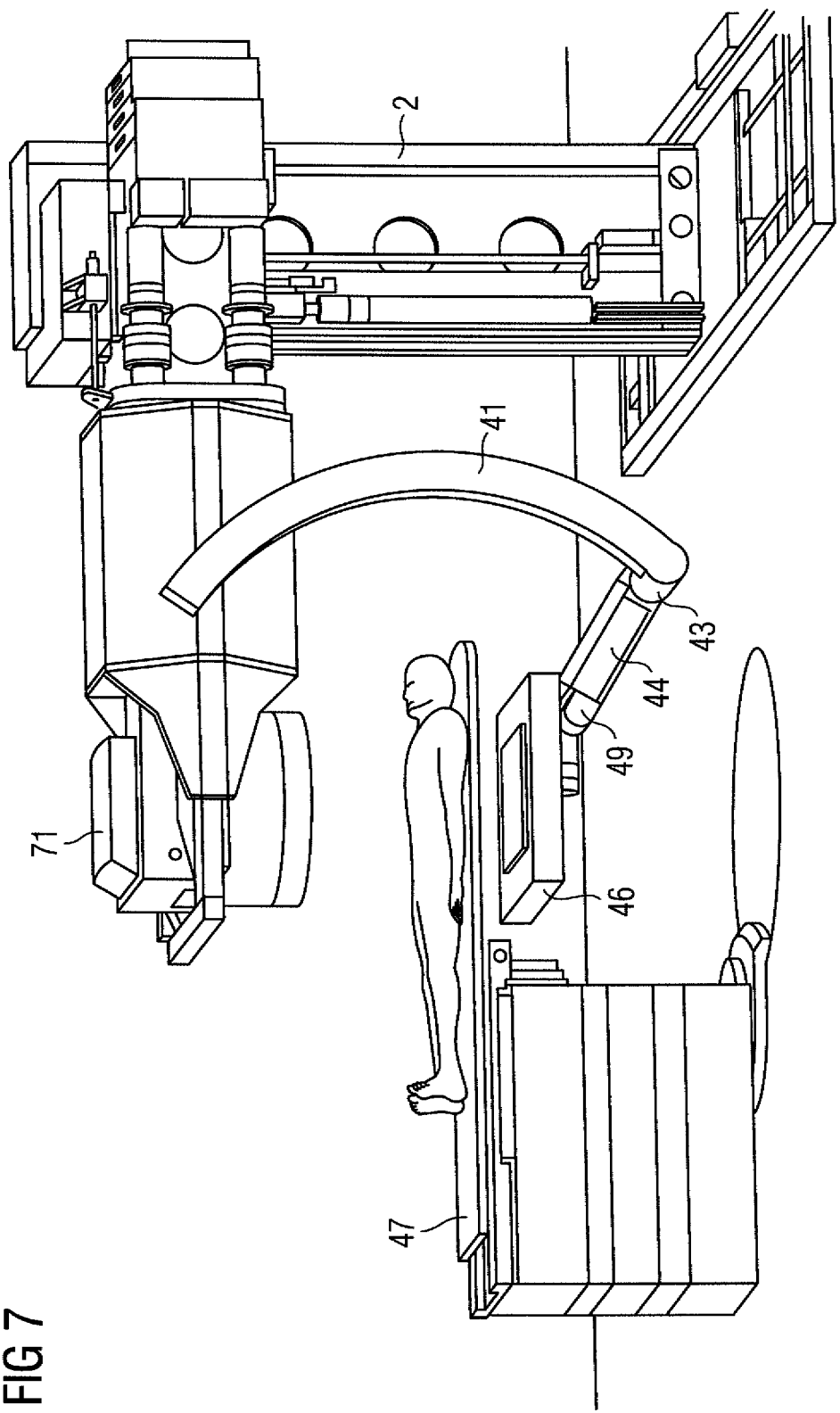
FIG. 7 shows one embodiment of the suspension system from FIG. 4 with one embodiment of a holding arm that supports a detector.

FIG. 7 shows the column structure from FIG. 4 with an emitter head 71. Cladding of the emitter head 71 is not shown in FIG. 4. The emitter head 71 is part of an emitter unit. A patient lies on a couch 47. In the embodiment shown in FIG. 7, the beam source is replaced by a detector 46 that registers radiation used during treatment and evaluates the radiation for diagnostic purposes (e.g., tumor position determination). In one embodiment, an additional joint 49 is provided in a region of the detector 46, so that the detector 46 may be tilted. This allows even more flexible positioning with the aid of the jointed arm segment 44.

Figure 8:
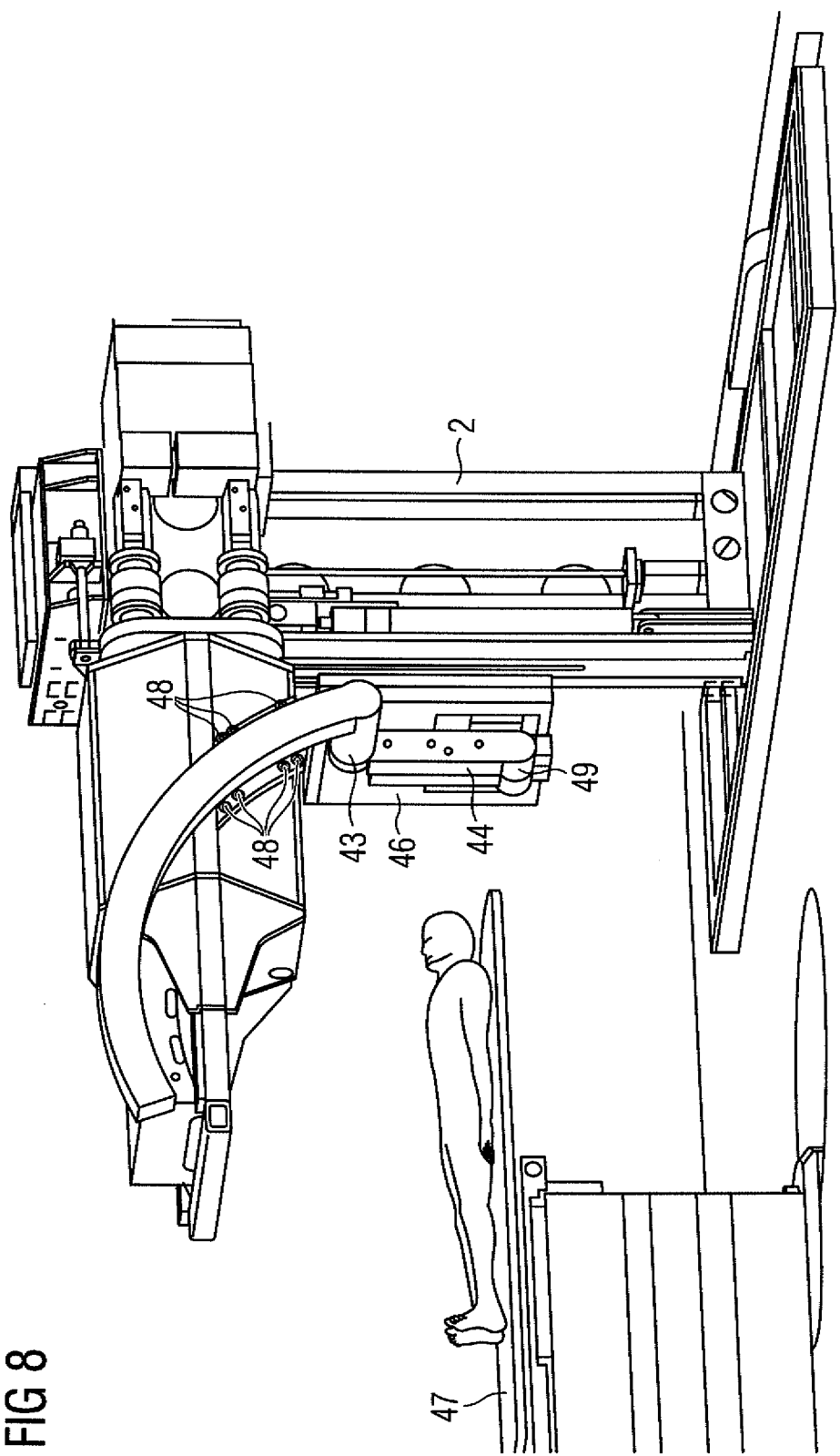
FIG. 8 shows one embodiment of a holding arm with a detector in a park position.
Figure 9:
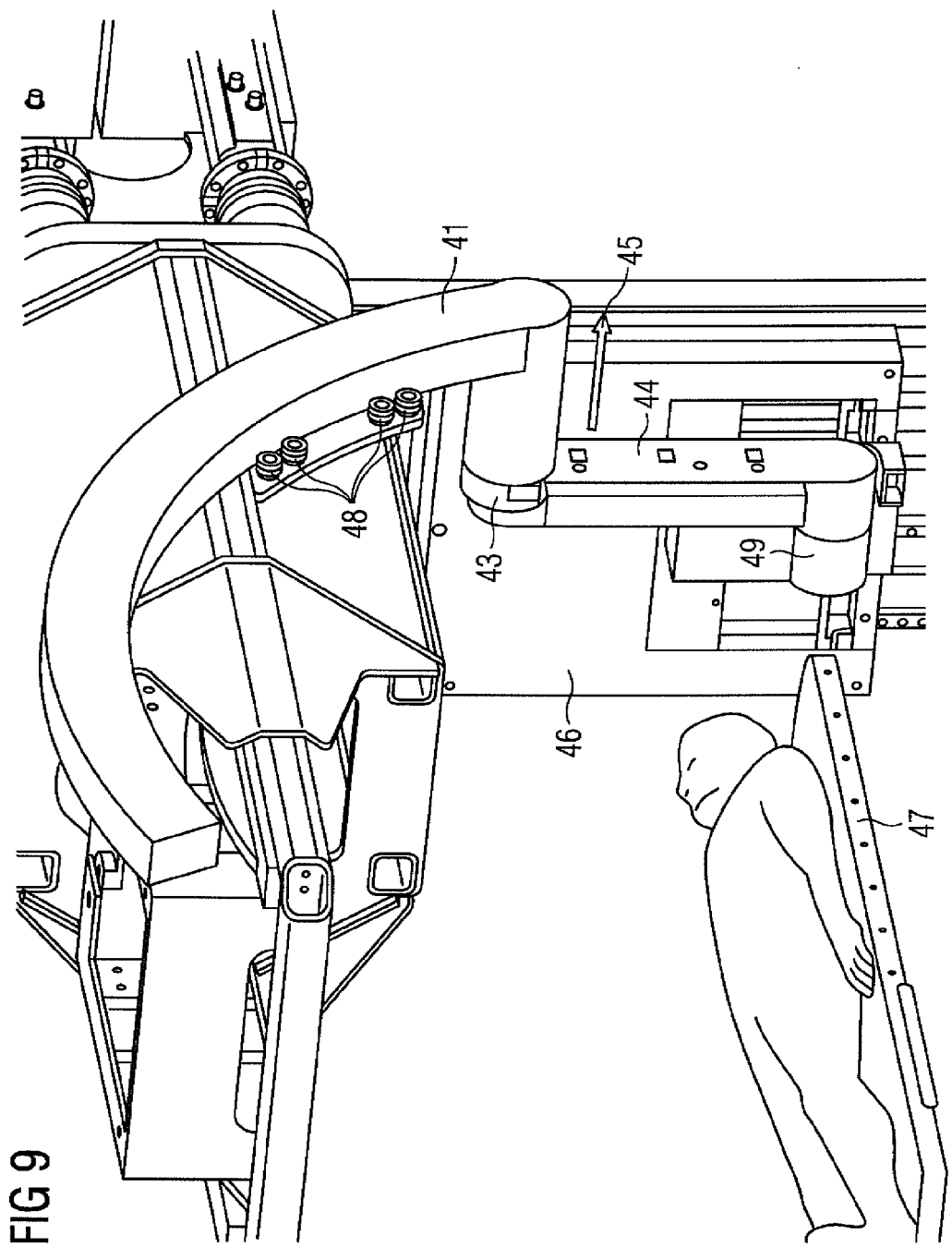
FIG. 9 shows an enlarged diagram of one embodiment of a holding arm with a detector in a park position.
Figure 10:
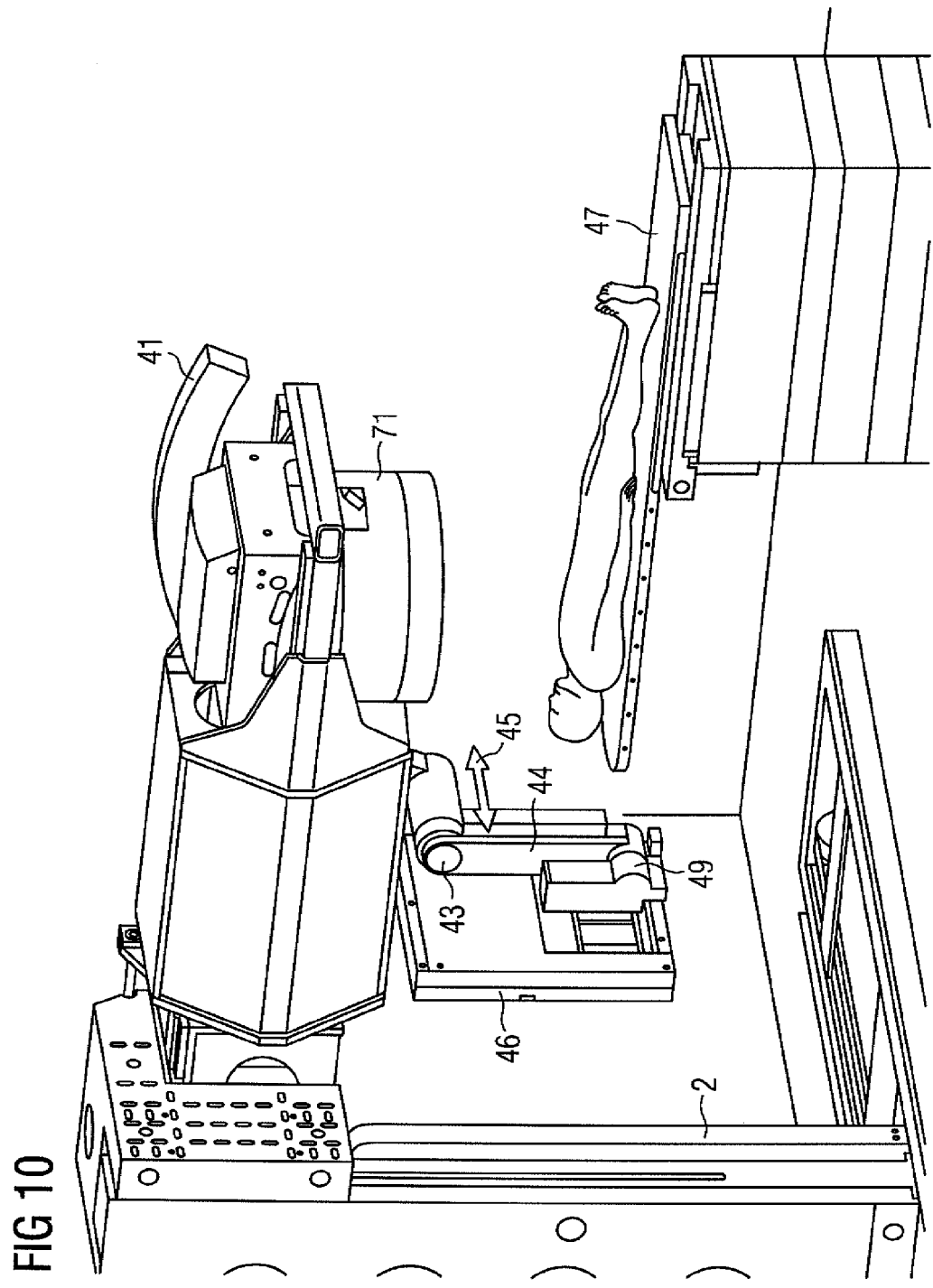
FIG. 10 shows one embodiment of a holding arm with a detector in a park position.

FIG. 8 shows the detector 46 in a park position. In the park position, the detector 46 is folded into a vertical position with the aid of the joint 43. The holding arm 41 is transported into the park position using a motor. The motor may be disposed at a side of the emitter unit, for example. A transport mechanism may be embodied using toothed belts and may include an energy chain. The holding arm 41 may be supported, for example, using a ball joint. Guides 48 are provided for arc movement (or orbital movement) of the holding arm 41 into the park position. The guides 48 are shown more clearly in FIG. 9. In the embodiment shown in FIG. 9, four rollers are visible. The four rollers hold the holding arm 41 on an intended path. Corresponding rollers are provided on a rear. The corresponding rollers may be seen in FIG. 8, but in FIG. 9, the corresponding rollers are hidden by the holding arm 41. FIG. 10 shows another view of the holding arm 41 in the park position. An upper end of the holding arm 41 is located close to the emitter head 71. It is therefore easy to adapt any cladding with space for the emitter head 71 and the arm 41.

Figure 11:
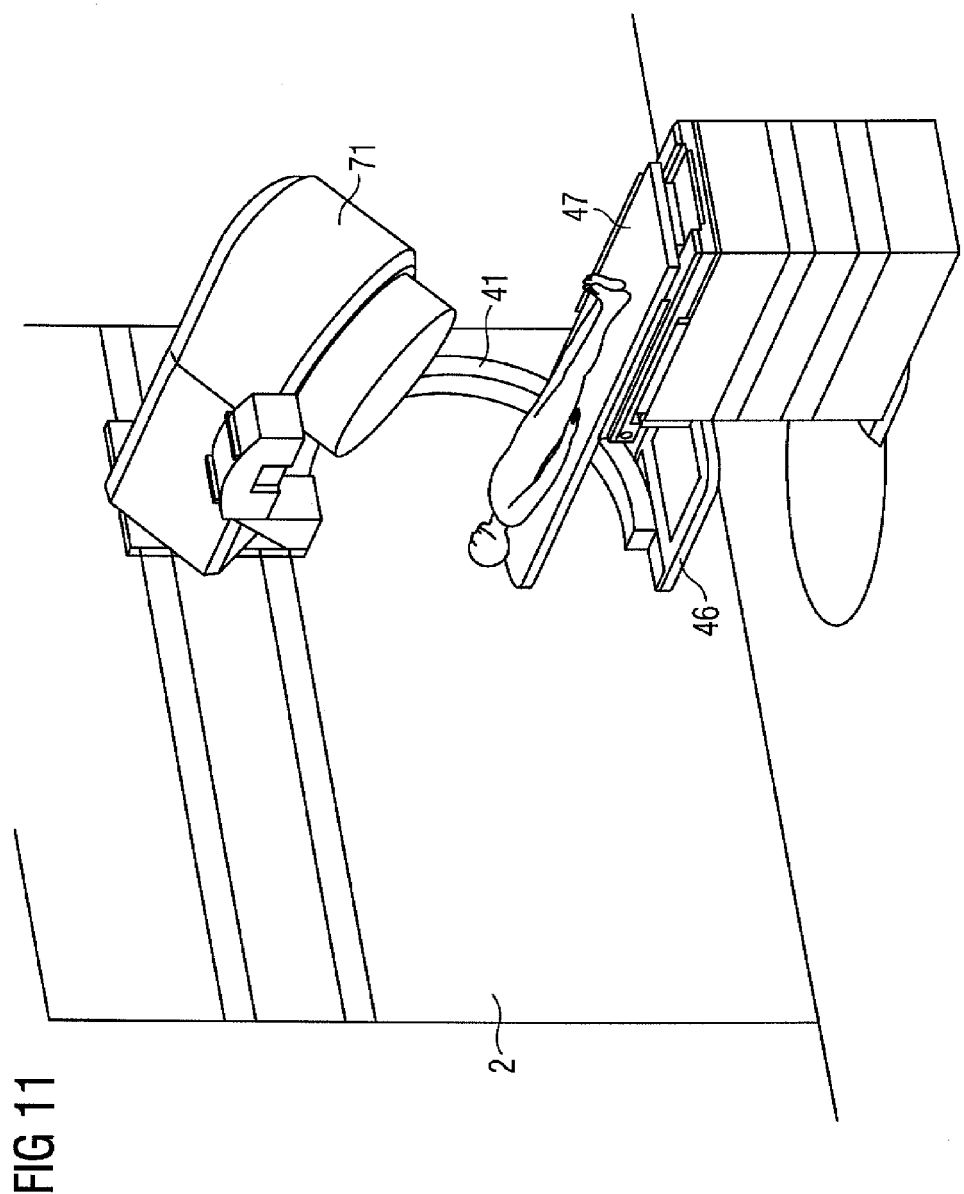
FIG. 11 shows one embodiment of a holding arm with 45° orientation in relation to the holding arms in the other figures.

The embodiments illustrated here are only examples. Other possible ways of employing or configuring embodiments of an arm as part of a therapy system (e.g., using a larger number of degrees of freedom or joints) are immediately evident to the person skilled in the art and part of the concept of the present embodiments. FIG. 11 shows an embodiment with a different orientation of the arm 41. The arm arc is in a plane perpendicular to the longitudinal extension of the emitter head 71. The arm arc is disposed between the head and the gantry or support column 2. The arm 41 may also be able to execute an upward arc movement into the park position.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A therapy radiation system comprising:
a gantry extending along a vertical axis;
an emitter head comprising cladding, wherein the emitter head is positioned on the gantry and has a longitudinal extension that extends along a horizontal axis from the gantry perpendicular to the vertical axis, the horizontal and vertical axes providing a horizontal-vertical plane;
a beam source;
a detector; and
a curved holding arm comprising (1) a first arm end having a first joint connected to a jointed arm segment, the jointed arm segment supporting the beam source or the detector, and (2) a second arm end, opposite the first arm end, positioned at the emitter head,
wherein the curved holding arm is configured to move into a park position along an arc movement of the curved holding arm, the first arm end moving in a direction toward the emitter head,
wherein the arc movement of the curved holding arm is within the horizontal-vertical plane or a plane parallel with the horizontal-vertical plane, and
wherein the curved holding arm is accommodated in the cladding of the emitter head in the park position.

2. The therapy radiation system as claimed in claim 1, wherein the first arm end of the curved holding arm abuts the emitter head in the park position.

3. The therapy radiation system as claimed in claim 1, wherein a rotation axis of the first joint is oriented horizontally and perpendicular to a direction defined by the longitudinal extension of the emitter head from the gantry.

4. The therapy radiation system as claimed in claim 1, wherein the jointed arm segment is offset in a direction of the rotation axis.

5. The therapy radiation system as claimed in claim 1, wherein the jointed arm segment comprises first and second ends, wherein the first arm end of the curved holding arm is connected to the jointed arm segment at the first end of the jointed arm segment, and wherein the second end of the jointed arm segment is connected to the beam source or the detector.

6. The therapy radiation system as claimed in claim 5, wherein a second joint is provided at the second end of the jointed arm segment to support the beam source or the detector.

7. The therapy radiation system as claimed in claim 1, wherein the system is configured for in-line imaging.

8. The therapy radiation system as claimed in claim 1, wherein the curved holding arm is positioned at a side of the emitter head.

9. The therapy radiation system as claimed in claim 1, wherein the detector or the beam source is movable into the park position.

10. The therapy radiation system as claimed in claim 1, further comprising a patient couch positioned between the detector and the beam source, wherein the longitudinal extension of the emitter head is parallel to a longitudinal direction of the patient couch.

11. The therapy radiation system as claimed in claim 1, further comprising guides positioned on or within the emitter head, wherein the curved holding arm is configured to move into the park position along the guides.

12. The therapy radiation system as claimed in claim 11, wherein the guides are rollers.

13. The therapy radiation system as claimed in claim 1, further comprising a motor, wherein the holding arm is configured to move into the park position using the motor.

14. The therapy radiation system as claimed in claim 1, further comprising a transport mechanism having a toothed belt, wherein the holding arm is configured to move into the park position using the transport mechanism.

15. A therapy radiation system comprising:
a gantry;
an emitter head positioned on the gantry, the emitter head comprising cladding;
a beam source;
a detector; and
a curved holding arm comprising (1) a first arm end having a first joint connected to a jointed arm segment, the jointed arm segment supporting the beam source or the detector, and (2) a second arm end, opposite the first arm end, positioned at the emitter head,
wherein the curved holding arm is configured to move into a park position along an arc movement of the curved holding arm, the first arm end moving in a direction toward the emitter head such that the first arm end abuts the emitter head in the park position,
wherein the entire curved holding arm is accommodated in the cladding of the emitter head in the park position except for the first arm end abutting the emitter head.

* * * * *